(12) United States Patent
Aldhafeeri

(10) Patent No.: US 10,299,813 B2
(45) Date of Patent: May 28, 2019

(54) SURGICAL APPARATUS FOR ENDOSCOPIC INFERIOR TURBINATE LATERALIZATION

(71) Applicant: Hamed Obaid Aldhafeeri, Al Dhahran (SA)

(72) Inventor: Hamed Obaid Aldhafeeri, Al Dhahran (SA)

(*) Notice: Subject to any disclaimer, the term of this patent is extended or adjusted under 35 U.S.C. 154(b) by 367 days.

(21) Appl. No.: 15/401,764

(22) Filed: Jan. 9, 2017

(65) Prior Publication Data

US 2018/0193047 A1 Jul. 12, 2018

(51) Int. Cl.
| | |
|---|---|
| A61B 17/24 | (2006.01) |
| A61B 1/233 | (2006.01) |
| A61M 29/00 | (2006.01) |
| A61B 17/02 | (2006.01) |
| A61B 1/00 | (2006.01) |
| A61B 90/00 | (2016.01) |

(52) U.S. Cl.
CPC ............. *A61B 17/24* (2013.01); *A61B 1/233* (2013.01); *A61B 17/0206* (2013.01); *A61M 29/00* (2013.01); *A61B 1/00016* (2013.01); *A61B 1/00018* (2013.01); *A61B 1/00045* (2013.01); *A61B 17/0218* (2013.01); *A61B 2090/033* (2016.02)

(58) Field of Classification Search
CPC ................ A61B 17/24; A61B 18/1442; A61B 2018/145; A61B 2018/00327
See application file for complete search history.

(56) References Cited

U.S. PATENT DOCUMENTS

| | | | | |
|---|---|---|---|---|
| 252,306 | A | * | 1/1882 | Ewing ............ A61B 17/320016 606/175 |
| 4,385,628 | A | * | 5/1983 | Straith ............... A61B 17/1688 606/174 |
| 7,588,570 | B2 | * | 9/2009 | Wakikaido ......... A61B 18/1442 606/52 |
| 8,475,454 | B1 | | 7/2013 | Alshemari |
| 2008/0027423 | A1 | | 1/2008 | Choi et al. |
| 2011/0160740 | A1 | | 6/2011 | Makower et al. |
| 2014/0276988 | A1 | | 9/2014 | Tagge et al. |
| 2015/0297285 | A1 | | 10/2015 | Wolf et al. |

FOREIGN PATENT DOCUMENTS

CN 102670279 A 9/2012

* cited by examiner

*Primary Examiner* — Andrew Yang
(74) *Attorney, Agent, or Firm* — Oblon, McClelland, Maier & Neustadt, L.L.P.

(57) ABSTRACT

A surgical apparatus is provided for performing turbinate lateralization including a pair of levers connected at a fulcrum, each lever including a handle connected to a bend portion, a pair of shafts, each shaft connected to the bend portion of each of the levers on first side of the fulcrum, where each shaft is dilated laterally with a substantially parallel displacement along a shaft length in response to the pair of levers being brought together on a second side of the fulcrum; a limiter connected to the pair of levers and configured to limit a dilation of the pair of levers in response to the pair of levers being brought together on the second side of the fulcrum; and a limiting bridge configured to attach between the shafts at a predetermined distance from the distal end of each shaft and press against a columella of the patient.

20 Claims, 6 Drawing Sheets

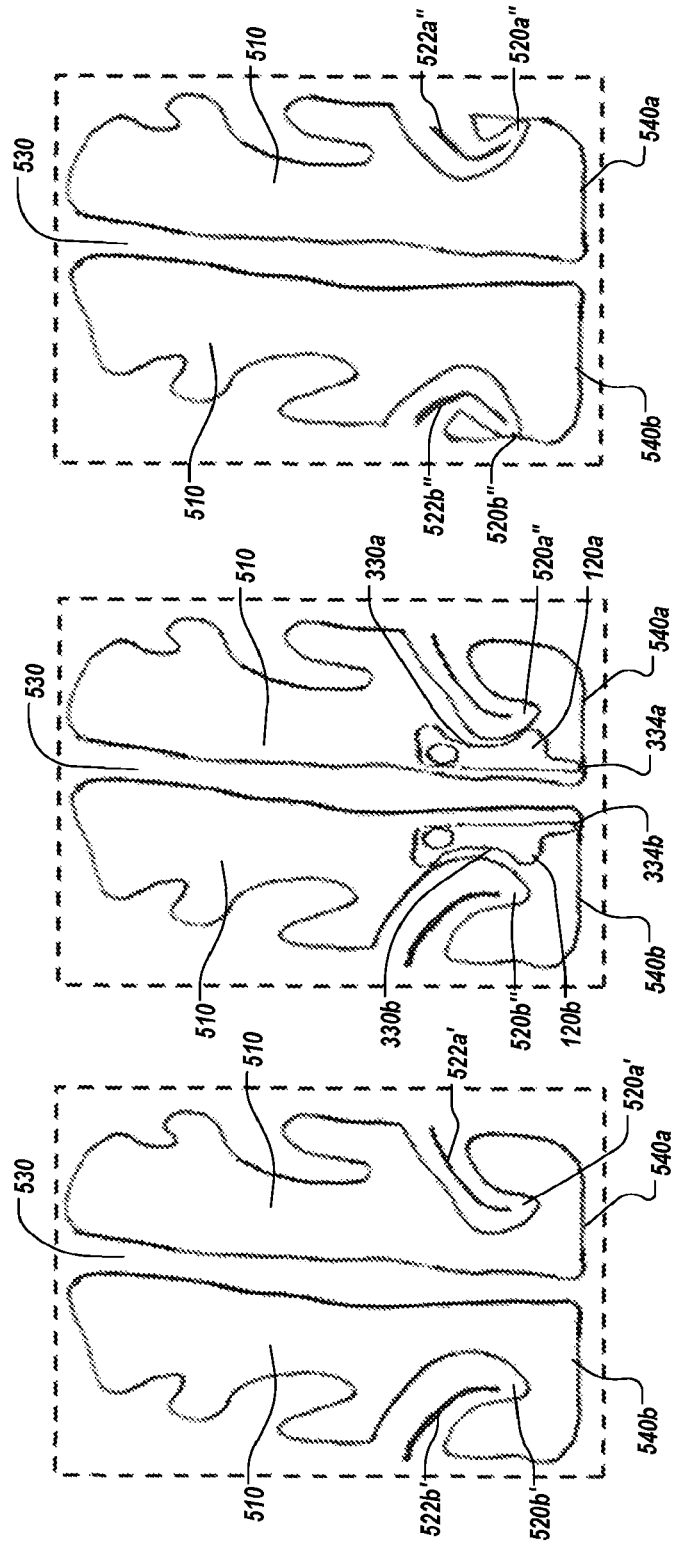

SURGICAL APPARATUS FOR ENDOSCOPIC INFERIOR TURBINATE LATERALIZATION

BACKGROUND

A common cause of nasal obstruction is narrow nasal passages within a nasal cavity. Narrow nasal passages can be due to common problems with a nasal septum, turbinates and sinuses of the nose. The nasal septum is a structure that divides the nasal passages into right and left sides. The turbinates are located on the infero-lateral walls of the nasal cavity. When the turbinates are too large they can cause nasal obstruction, snoring, rhinosinusitis and obstructive sleep apnea. Inferior turbinates most commonly affect airflow of the nasal passages. Airflow of the nasal passages can be improved by reducing a size of the inferior turbinates tissues (turbinectomy) and by altering a position of inferior conchal bone and its erectile tissues or turbinates (inferior turbinate lateralization) to allow more air flow while keeping natural functions of the tubinates.

The traditional surgical procedure for performing inferior turbinate lateralization results in bleeding as the inferior turbinates are highly vascular. Electrical burning of tissues (cautery) is required stop such bleeding. Consequently, pediatric patients cannot go for turbinate reduction surgeries, while lateralization is a good and safe choice. In addition, patients with cardiac issues including patients having a pacemaker can't undergo the surgical excision procedures which may need cauterization. This disclosure relates to a surgical instrument in the field of rhinology and maxillofacial surgery for performing inferior turbinate lateralization.

SUMMARY

A surgical apparatus is provided for performing inferior turbinate lateralization including a pair of levers connected at a fulcrum, each lever including a handle connected to a bend portion, a pair of shafts, each shaft connected to the bend portion of each of the levers on first side of the fulcrum, where each shaft is dilated laterally with a substantially parallel displacement along a shaft length in response to the pair of levers being brought together on a second side of the fulcrum, and the pair of shafts are configured to be inserted into a nasal cavity of a patient; a limiter connected to the pair of levers and configured to limit a dilation of the pair of levers in response to the pair of levers being brought together on the second side of the fulcrum; and a limiting bridge configured to attach between the shafts at a predetermined distance from the distal end of each shaft and press against a columella of the patient, where the predetermined distance is configured to limit intrusion of the shafts into a nasal cavity of the patient. Using the surgical apparatus, both turbinates can be lateralized simultaneously, under illuminated and visualized surgical field, without bleeding or need for cauterization. Further, the surgical procedure can be done in an operating room as well as an outpatient clinic or office.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 5A is a coronal view of the nasal cavity including a pair of inferior conchae that are narrowing the nasal cavity according to an example;

FIG. 5B is a coronal view of the nasal cavity including a placement of the cross-section of the shafts, as shown in FIG. 3B, against both inferior conchae of the nasal cavity according to an example; and FIG. 5C is a coronal view of the nasal cavity with the pair of inferior conchae that are lateralized, opening the nasal cavity according to an example.

DETAILED DESCRIPTION

Figure 1A:
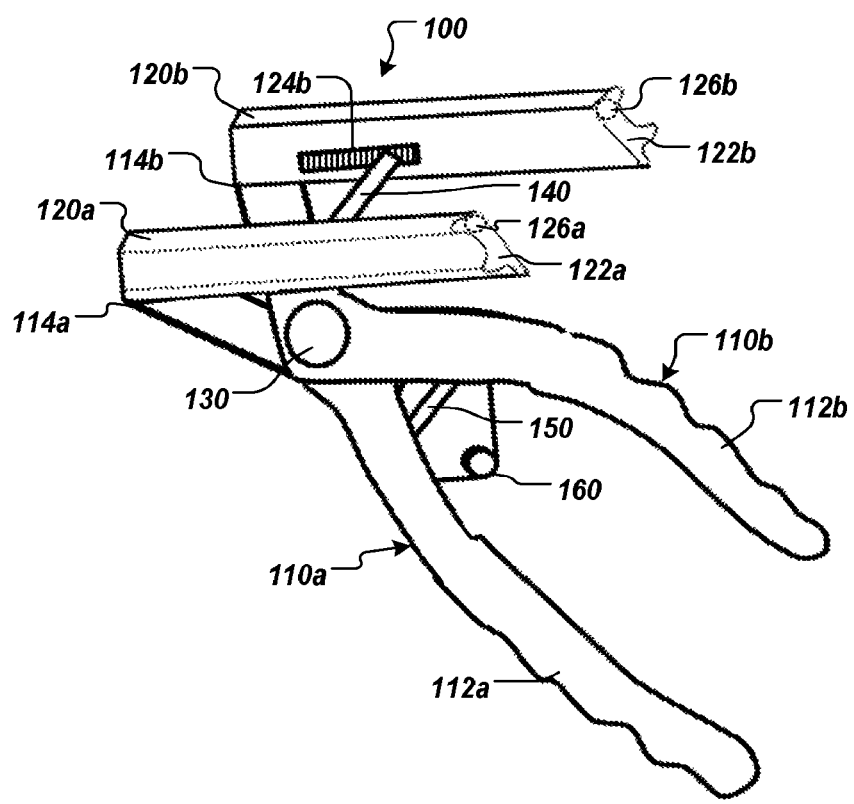
FIG. 1A is a perspective drawing of an surgical apparatus for performing inferior turbinate lateralization including a pair of levers connected at a fulcrum, each lever including a handle, a bending portion, and a shaft, where both shafts are connected with a limiting bridge configured to prevent excessive intrusion of the shafts into a nasal cavity of a patient according to an example.

This disclosure relates to a surgical instrument for performing inferior turbinate lateralization. During the procedure, two shafts of the surgical instrument are introduced into a nasal cavity of a patient and the shafts are expanded. The expanded shafts are configured to lateralize a pair of inferior turbinates of the patient. Using the surgical apparatus, both turbinates can be lateralized simultaneously, under illuminated and visualized surgical field, without bleeding or need for cauterization. Further, the surgical procedure can be done in an operating room as well as an outpatient clinic or office.

Referring now to the drawings, wherein like reference numerals designate identical or corresponding parts throughout the several views.

FIG. 1A is a perspective drawing of an surgical apparatus 100 for performing inferior turbinate lateralization including a pair of levers 110*a-b* connected at a fulcrum 130 and a limiting bridge 140, each lever 110*a-b* including a handle 112*a-b*, a bend portion 114*a-b*, and a shaft 120*a-b* according to an example. By pressing both handles 112a-b inward (medially), both shafts 120a-b are configured to move outward (laterally) to a maximum dilation on each side. In an example, the maximum dilation on each side can be set as 50 mm-80 mm for an adult patient.

In some implementations, each lever 110a-b is made into one piece. In an embodiment, each shaft 120a-b can be removeably connected to and replaced on the bend portion 114a-b. For example, a separate pair of shafts 120a-b can be configured for an adult patient and a pediatric patient. In an example, the shaft 120a-b configured for an adult patient can have a length of around 10-13 cm and a width of around 13 mm. In an example, the shafts 120a-b can have dimensions based on a nasal cavity of the pediatric patient. In another example, the shafts 120a-b can be based on dimensions of a naval cavity of a patient obtained through preoperative imaging techniques.

The surgical apparatus 100 further includes a limiter 150 configured to set a dilation limit of the pair of levers 110a-b. In an example, the limiter 150 can be used to prevent the shafts 120a-b from being over-dilated within the nasal cavity by restricting the maximum dilation of the shafts 120a-b (See FIGS. 1B-1C). In some implementations, the limiter 150 can have an adjustable dilation limit that can be configured to limit the maximum dilation of the pair of levers 110a-b based on the patient or the surgical procedure. In an example, the maximum dilation can be set based on preoperative images of the patient's nasal cavity. The dilation limit of the limiter 150 can be adjusted by adjusting a nut on a screw according to an example.

In an example, a spring 160 provides resistance during dilation of the levers 110a-b. For example, the spring 160 can be used to increase a force required to dilate the shafts 120a-b within the nasal cavity by adding resistance to separation of the pair of levers 110a-b below the fulcrum 130.

Figure 4:
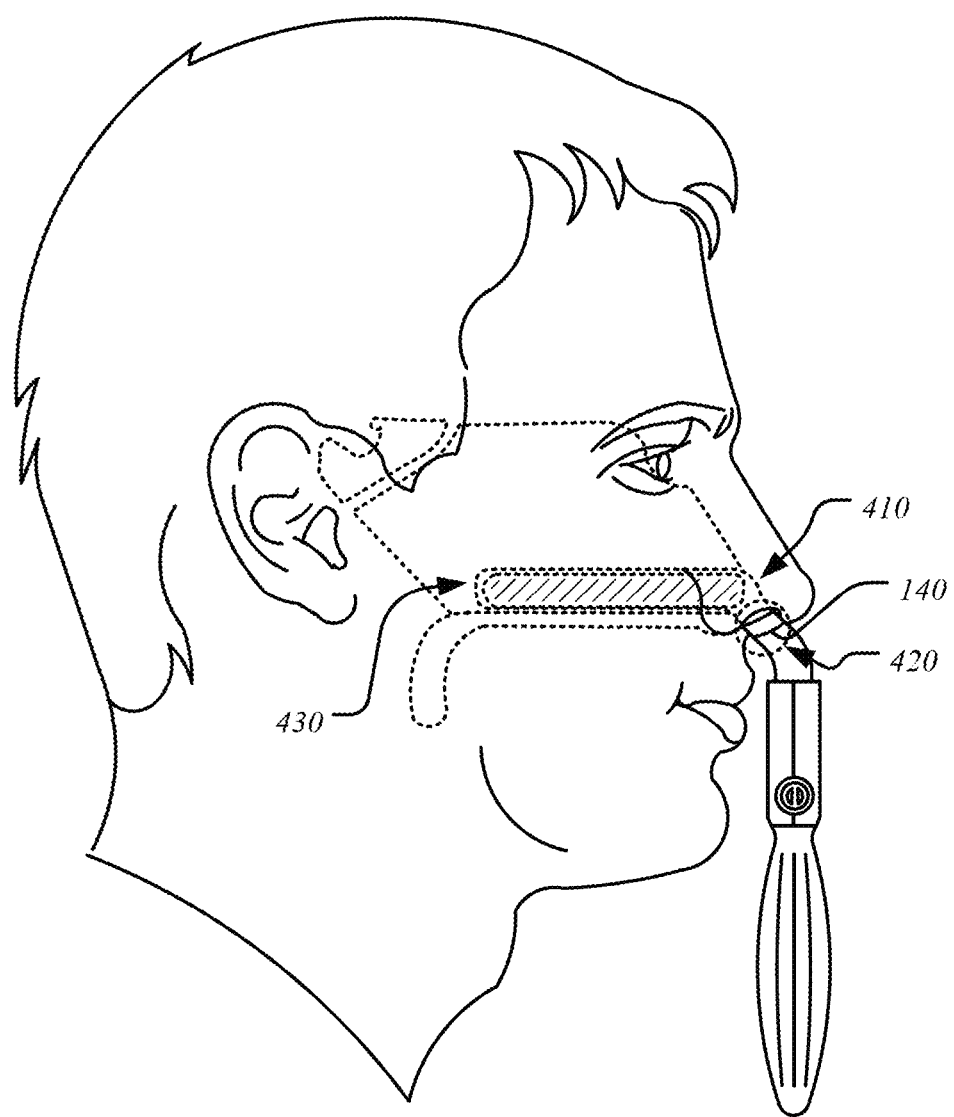
FIG. 4 is a side view of a lever inserted into a nasal cavity of a patient showing the shaft having a shape configured to complement an anatomical nasal contour according to an example.

In an example, the limiting bridge 140 can be used to prevent the shafts 120a-b from excessive intrusion by at least one shaft 120a-b into a nasal cavity of a patient by pressing a columella of a nose during insertion of the surgical apparatus 100 (See FIG. 4). In an example, each shaft 120a-b can have a channel defining a plurality of securing points 124a-b for the limiting bridge 140 along a length of each shaft 120a-b. The limiting bridge 140 is configured to removeably connect to each shaft 120a-b at a respective securing point 124a-b along a length of each shaft 120a-b. In an example, the securing point 124a-b can be set based on dimensions of a naval cavity of a patient obtained through preoperative imaging techniques.

In an aspect, the limiting bridge 140 can be configured to simultaneously prevent excessive intrusion of the shafts 120a-b as well as prevent over-dilation of the shafts 120a-b as described above for the limiter 150. In an example, in case of accidental release of the handles 112a-b, the limiting bridge 140 can prevent injury to the columella, the inferior turbinates, and the nasal septum of the patient. In an example, the limiting bridge 140 can further include a pressure sensor (not pictured) configured to detect a pressure applied by the limiting bridge 140 to the columella of the nose and a light or sound indicator (not shown) configured to alert the surgeon when the pressure applied is above a certain threshold.

Figure 3A:
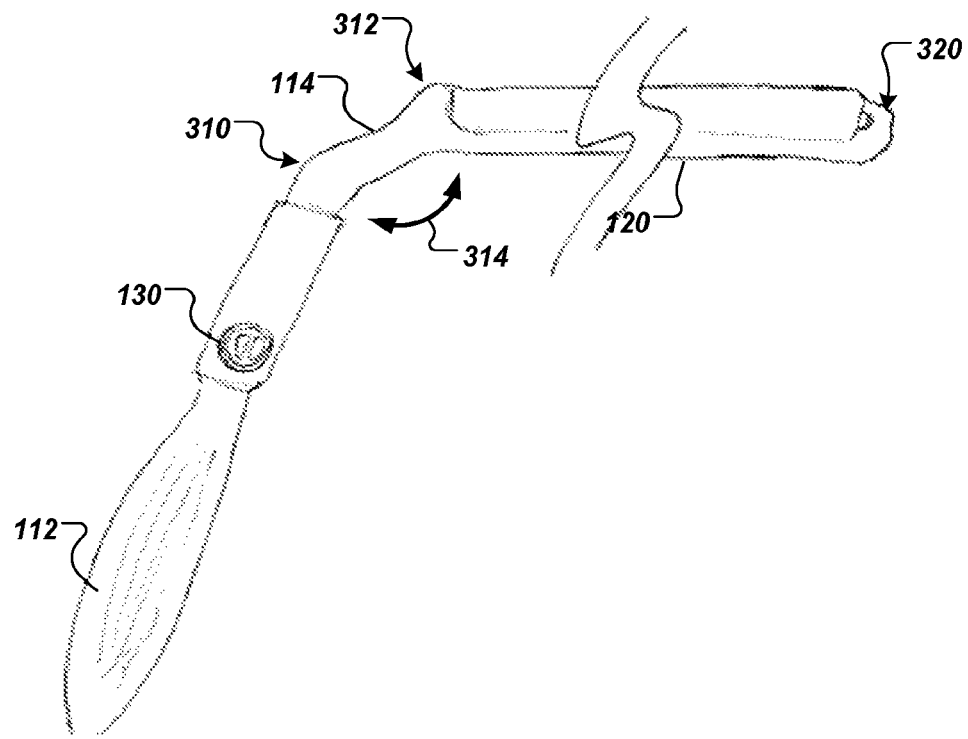
FIG. 3A is a side view of a lever showing the handle connected to the shaft with a bend portion according to an example.

In an example, each shaft 120a-b can include a blunt introducing tip 320 extending from a portion of a distal end of the shaft 120a-b (See FIG. 3A). The blunt introducing tip 320 can be configured to aid insertion of the shafts 120a-b as well as to protect nasal alar cartilage of the patient from injury during insertion.

Figure 1C:
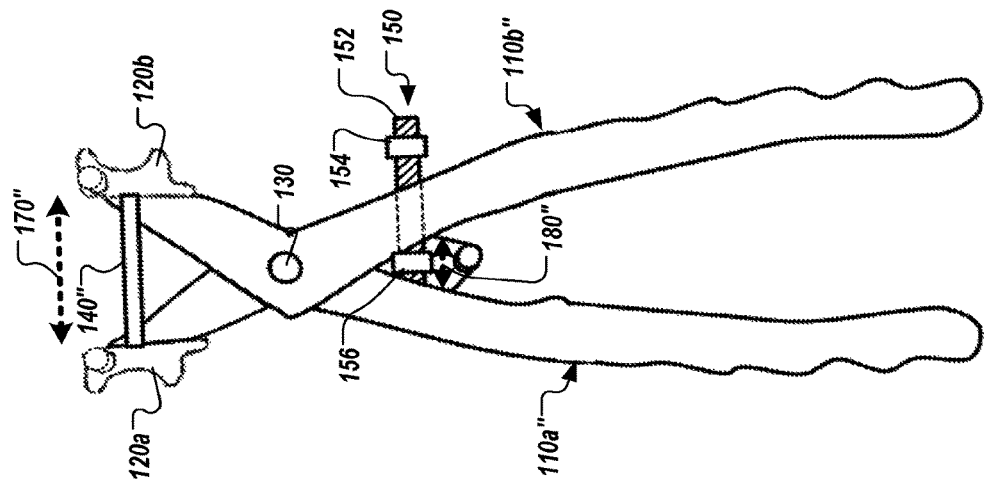
FIG. 1C is a front view of the surgical apparatus showing the pair of levers contracted and the shafts expanded from each other according to an example.
Figure 1B:
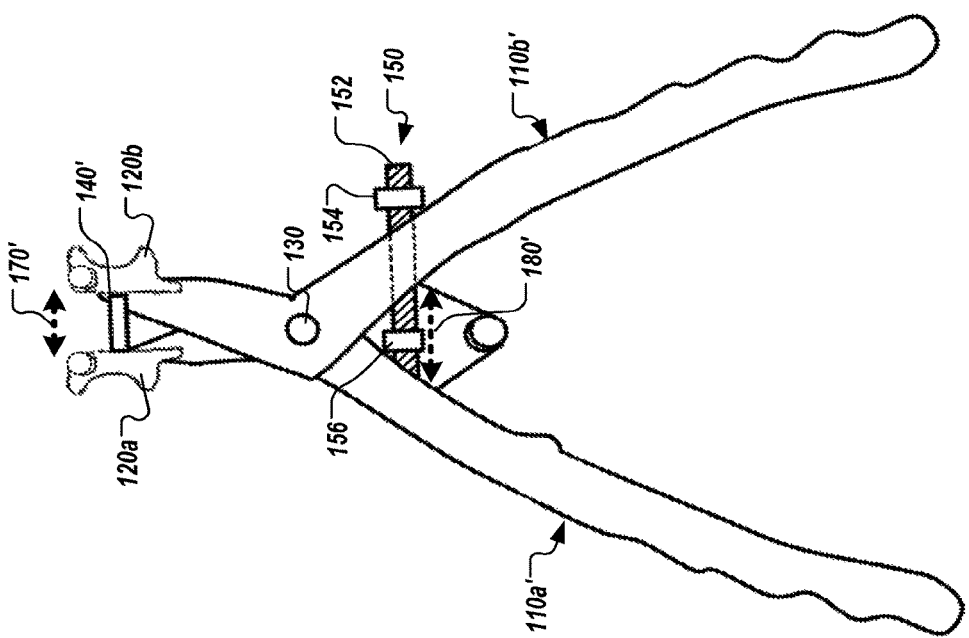
FIG. 1B is a front view of the surgical apparatus including a limiter configured to set a dilation limit of the pair of levers and showing the pair of levers expanded and the shafts adjacent to each other according to an example.

FIG. 1B is a front view of the surgical apparatus 100 showing the pair of levers 110a-b expanded or dilated at the limiter 150 with a distance 180' and the shafts 120a-b adjacent to each other with a distance 170' according to an example. In an example, the limiter 150 can include a screw 152, an external stopper 154, and an internal stopper 156. When the pair of levers 110a-b are dilated below the fulcrum 130, the shafts 120a-b are collapsed to a minimum distance that also prevents damage to the septum 530 of the patient (See FIGS. 5A-5B). The dilation of the pair of levers 110a-b can be limited by the external stopper 154 hitting the lever 110b according to an example.

FIG. 1C is a front view of the surgical apparatus 100 showing the pair of levers 110a-b contracted at the limiter 150 with a distance 180" and the shafts 120a-b expanded from each other with a distance 170". When the pair of levers 110a-b are contracted below the fulcrum 130, the shafts 120a-b are expanded to a maximum distance for performing the lateralization procedure. In an example, the maximum distance on each side of the nose (half distance 170") for an adult patient is between 5 mm to 10 mm and 3 mm to 6 mm for a pediatric patient. The contraction of the pair of levers 110a-b can be limited by the internal stopper 156 hitting the lever 110a according to an example.

Endoscope Enabled

Figure 2A:
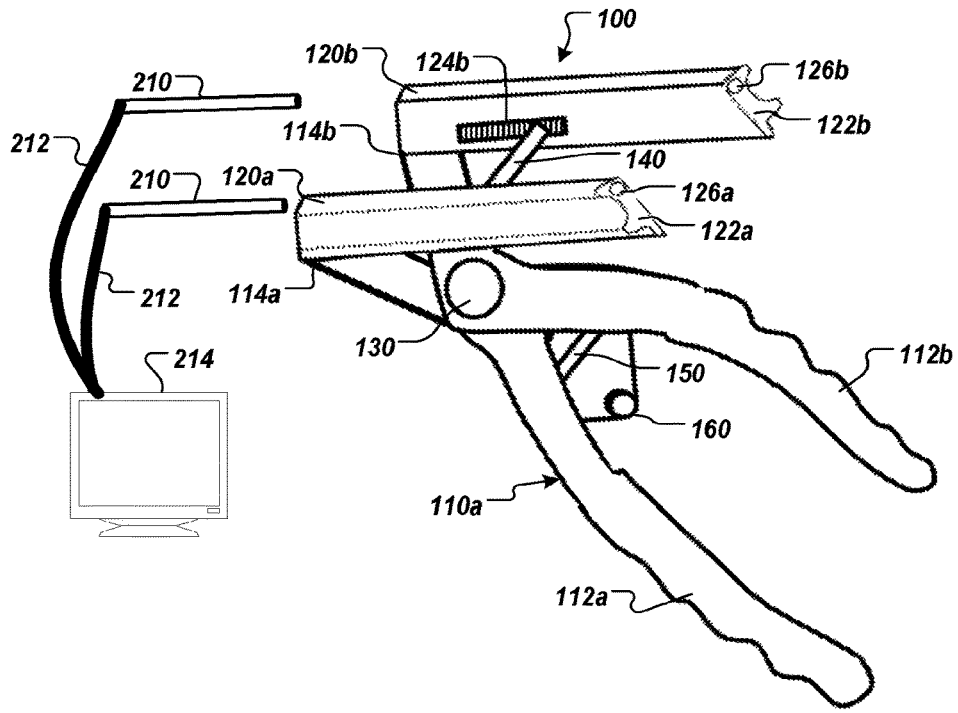
FIG. 2A is a drawing showing a system for performing inferior turbinate lateralization including the surgical apparatus configured to receive a pair of removable endoscopes configured to connect to a display for aiding viewing during a surgery according to an example.
Figure 2B:
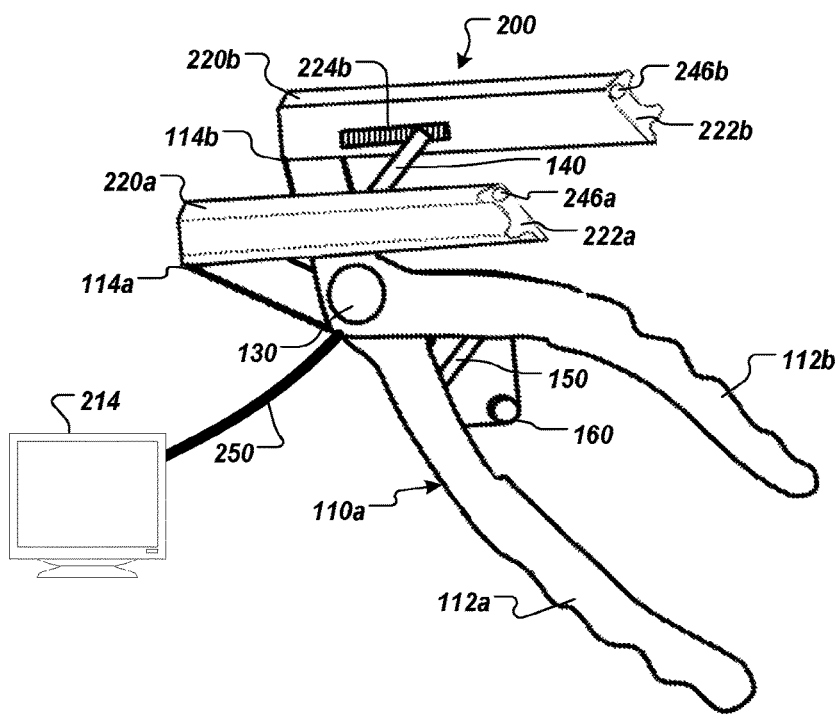
FIG. 2B is a drawing showing a system for performing inferior turbinate lateralization including a surgical apparatus having an endoscope configured to connect to a display according to an example.

As shown in FIGS. 2A-2B, in some implementations, the surgical apparatus can include a pair of endoscopes for viewing in the nasal cavity during use of the surgical apparatus 100. In an example, each endoscope can be configured to provide a viewing angle of insertion and the surgical field (e.g., 90 degree and higher), illumination, as well as for documentation and recording for teaching purposes. In an example, each endoscope can be configured to illuminate the surgical field. Alternatively, each shaft can include a separate light source (not shown).

In an example, each shaft 120a-b of the surgical apparatus 100 can have a conduit 126a-b configured to receive a removable endoscope 210 that can be connected to an external display 214. The removable endoscope 210 can be connected to the external display 214 by a cable or wirelessly. The removable endoscope 210 can be a commercially available endoscope/sinuscope where a working length of the endoscope is introduced into a portion of the surgical apparatus 100 prior to use. An example of the removable endoscope 210 can be a DE1250 Wireless Video Endo-Camera from Firefly Global, LLC (Belmont, Mass.).

In another example, as shown in FIG. 2B, a surgical apparatus 200 can include one or more embedded endoscopes 246. The surgical apparatus 200 can include other features as described for the surgical apparatus 100 such as the pair of levers 110a-b connected at the fulcrum 130, the limiting bridge 140, where each lever 110a-b includes a handle 112a-b, a bend portion 114a-b, and a shaft 220a-b. Each shaft 220a-b can include an embedded endoscope 246 configured to connect to a display 214. In an example, a cable 250 can be used to connect each embedded endoscope 246 to the external display 214. In an example, the cable 250 can be a flexible fiber optic cable that can be routed within the surgical apparatus 100, 200. For instance, the cable 250 can exit the surgical apparatus 100, 200 at the fulcrum 130 or at different parts of the pair of levers 110a-b. Alternatively, the embedded endoscopes 246 can be connected to the external display 214 wirelessly.

Bend Portion

FIG. 3A is a side view of a lever 110*a-b* including the bend portion 114*a-b* having a proximal end with a first bend angle 310 connected to the handle 112*a-b* and a distal end with a second bend angle 312 connected to the shaft 120*a-b*. FIG. 4 is a side view of a lever 110*a-b* inserted into a nasal cavity of a patient showing the shaft 120*a-b* having a shape configured to complement an anatomical nasal contour according to an example. In an example, the first bend angle 310 is configured to prevent injury to the nasal dorsum of the patient, as best shown at 420 in FIG. 4. In an example, the second bend angle 312 is configured to prevent injury to the lower alar cartilage of the patient, as shown at 410 in FIG. 4.

The shafts 120*a-b* can be configured for an adult patient and a pediatric patient. In an example, the shaft 120*a-b* configured for an adult patient can have a length of around 10-13 cm and a width of around 13 mm. In an example, the shafts 120*a-b* can be replaced on the bend portion 114*a-b* and configured for the pediatric patient. As shown at 430, a distal end of the shaft 120*a-b* is configured to reach a posterior end of the turbinate, while also not exceeding beyond the turbinate where another bony structure can change the force applied during the procedure. In an example, each shaft 120*a-b* is configured to provide substantially equal pressure along the length of the turbinate. In an example, the distal end of the shaft 120*a-b* has a blunt tip with a curved edge to prevent injury to tissue during introduction of the shafts 120*a-b*. In an example, a shaft length for an adult patient can be around 70 mm and for a pediatric patient around 40 mm long. In an example, the first bend angle 310 and the second bend angle 312 can be configured such that the bend portion 114*a-b* has a combined angle 314 of about 60°. In an aspect, the combined angle 314 of the bend portion 114*a-b* is configured to translate the movement of the pair of levers 110*a-b* at the fulcrum 130 into a parallel displacement along the length of the shaft 120*a-b* as shown in FIG. 1C. In an example, the fulcrum 130 can be shaped as a ring with an opening for a thumb or finger to aid in maneuverability.

Shaft Anatomical Shape

Figure 3B:
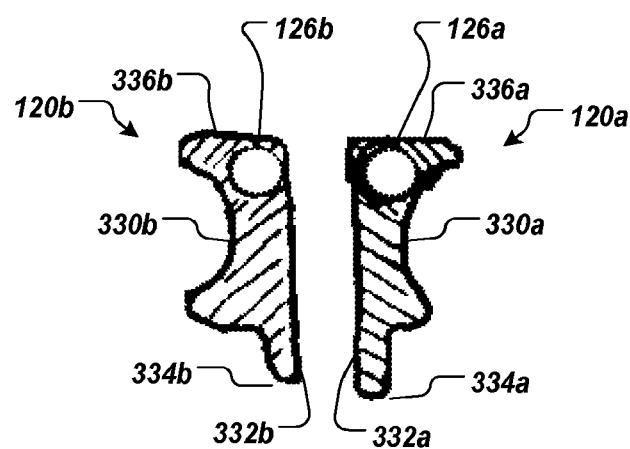
FIG. 3B shows a cross-section of the shafts where a first (left) shaft has a straight medial surface, a curved lateral surface, a narrow inferior surface, and a flat superior surface and a second (right) shaft has a mirror image relative to the midline according to an example.

In an aspect, each shaft 120*a-b* is configured to have a shape matching a respective surface of the anatomical nasal contour according to an example. FIG. 3B shows a cross-section of the shafts 120*a-b* oriented into a right shaft 120*a* and a left shaft 120*b*. The shafts 120*a-b* can have complementary shapes that are a mirror image to each other relative to a midline according to an example. In an example, the right shaft 120*a* includes a straight medial surface 332*a*, a curved lateral surface 330*a*, a narrow inferior surface 334*a*, and a flat superior surface 336*a*. In an example, the left shaft 120*b* has a straight medial surface 332*b*, a curved lateral surface 330*b*, a narrow inferior surface 334*b*, and a flat superior surface 336*b*.

FIG. 5A is a coronal view of a nasal cavity 510 including the septum 530 dividing the nasal cavity 510 into a left side and a right side, a pair of inferior conchae 520*a'-b'*, and a left and right palate 540*a-b*. Each has an inferior conchal bone 522*a'-b'*. FIG. 5B also shows the coronal view of the nasal cavity 510 including the cross-section of the shafts 120*a-b*, as shown in FIG. 3B, lateralizing the pair of inferior conchae 520*a"-b"* according to an example. As shown in FIG. 5B, each curved lateral surface 330*a-b* is configured to interface with an inferior concha 520*a'-b'*. In an aspect, a curvature of each curved lateral surface 330*a-b* is configured to fracture each inferior conchal bone 522*a'-b'* and lateralize each inferior concha 520*a'-b'* while maintaining a general curved shape which can affect flow of air through the nasal cavity 510. In an aspect, the shape of each shaft 120*a-b* is configured to protect each respective interfacing cartilage from injury during the surgical procedure.

Once the surgical apparatus 100 is positioned within the nasal cavity 510, the surgical procedure can be performed by pressing both handles 112*a-b* inward (medially) such that both shafts 120*a-b* move outward (laterally). With sufficient force applied, the outward movement of the shafts 120*a-b* results in a pressure to the mucosa of the inferior turbinates leading to fracturing of the pair of inferior conchal bones 522*a-b* on both sides simultaneously. By avoiding penetration of underlying tissue a risk of external bleeding is reduced and even eliminated. FIG. 5C is a coronal view of the nasal cavity 510 with the pair of inferior conchal bones 522*a"-b"* fractured and the pair of inferior conchae 520*a"-b"* that have been lateralized, thereby opening the nasal cavity 510 according to an example.

Advantages

In an example, using the surgical apparatus 100 for performing inferior turbinate lateralization can result in an easier and less complicated surgery. Using the surgical apparatus 100 can avoid asymmetric lateralization, provide an ability to visualize blind spots, as well as reduce surgical time and bleeding. Performing inferior turbinate lateralization using the surgical apparatus 100 can be done in a bloodless procedure allowing for inclusion of patients with cardiac issues as well as pediatric patients or patients with comorbidity or bleeding diseases. In an aspect, performing inferior turbinate lateralization using the surgical apparatus 100 will not alter, change, or excise any normal tissue or physiology of the inferior turbinates.

The surgical apparatus 100 allows for performing lateralization on the inferior turbinates in both nasal cavities simultaneously, resulting in completion of the surgical procedure on both sides under fully illuminated and visualized surgical fields within few seconds. Further, using the surgical apparatus 100 can allow for the inferior turbinate lateralization procedure to be performed in an outpatient setting using local anesthesia or under general anesthesia in the operating room, for increased time efficiency, cost effectiveness, and reduced risk to the patient.

Obviously, numerous modifications and variations of the present disclosure are possible in light of the above teachings. It is therefore to be understood that within the scope of the appended claims, the invention may be practiced otherwise than as specifically described herein.

The invention claimed is:

1. An surgical apparatus for performing inferior turbinate lateralization, the surgical apparatus comprising:
   a pair of levers connected at a fulcrum, each lever including a handle connected to a bend portion having a first bend angle at a proximal end of the bend portion and a second bend angle at a second end of the bend portion,
   a pair of shafts, each shaft connected to the bend portion of each of the levers on first side of the fulcrum, wherein each shaft is dilated laterally with a substantially parallel displacement along a shaft length in response to the pair of levers being brought together on a second side of the fulcrum, and the pair of shafts are configured to be inserted into a nasal cavity of a patient;

a limiter connected to the pair of levers on the second side of the fulcrum and configured to limit a dilation of the pair of levers in response to the pair of levers being brought together on the second side of the fulcrum; and a limiting bridge configured to attach between the shafts at a predetermined distance from the distal end of each shaft and press against a columella of the patient, wherein the predetermined distance is configured to limit intrusion of the shafts into a nasal cavity of the patient.

2. The surgical apparatus of claim 1, further comprising: a spring connected to each lever below the fulcrum, the spring configured to resist dilation of the levers.

3. The surgical apparatus of claim 1, wherein the distal end of each shaft includes a blunt introducing tip configured to protect a nasal alar cartilage of the patient from injury during insertion of the shafts into the nasal cavity.

4. The surgical apparatus of claim 1, wherein each shaft has a straight medial surface complementing a shape of a septum of the nasal cavity, a curved lateral surface complementing a shape of an inferior concha of the nasal cavity, and an inferior surface configured to press against a palate of the nasal cavity, wherein, when sliding the inferior surface of each shaft on the palate of the nasal cavity, each curved lateral surface of each shaft is positioned adjacent to a respective inferior concha.

5. The surgical apparatus of claim 1, wherein the limiting bridge is configured to limit dilation of the shafts to less than or equal to a dilation limit between nostrils of the patient.

6. The surgical apparatus of claim 1, wherein the limiter is configured to limit collapsing of the handles, wherein the shafts are prevented from dilating beyond a dilation limit between nostrils of the patient.

7. The surgical apparatus of claim 1, wherein the first bend angle of the bend portion is configured to prevent injury to a nasal dorsum of the patient and the second bend angle of the bend portion is configured to prevent injury to a lower alar cartilage of the patient.

8. The surgical apparatus of claim 1, wherein each shaft includes a conduit configured to receive an endoscope.

9. The surgical apparatus of claim 1, wherein each shaft further includes an endoscope configured to provide a view of a surgical field at the distal end of each shaft.

10. The surgical apparatus of claim 9, wherein the endoscope is configured to connect wirelessly to a display.

11. An surgical assembly for performing inferior turbinate lateralization, the surgical assembly comprising:

a surgical apparatus including
a pair of levers connected at a fulcrum, each lever including a handle connected to a bend portion having a first bend angle at a proximal end of the bend portion and a second bend angle at a second end of the bend portion,
a pair of shafts, each shaft connected to the bend portion of each of the levers on first side of the fulcrum, wherein each shaft is dilated laterally with a substantially parallel displacement along a shaft length in response to the pair of levers being brought together on a second side of the fulcrum, and the pair of shafts are configured to be inserted into a nasal cavity of a patient, a limiter connected to the pair of levers on the second side of the fulcrum and configured to limit a dilation of the pair of levers in response to the pair of levers being brought together on the second side of the fulcrum, and a limiting bridge configured to attach between the shafts at a predetermined distance from the distal end of each shaft and press against a columella of the patient, wherein the predetermined distance is configured to limit intrusion of the shafts into a nasal cavity of the patient; and a pair of endoscopes, each endoscope having a working portion configured to fit within the conduit of each shaft, wherein the pair of endoscopes are configured to be connected to a display.

12. The surgical assembly of claim 11, further comprising: a spring connected to each lever below the fulcrum, the spring configured to resist dilation of the levers.

13. The surgical assembly of claim 11, wherein the distal end of each shaft includes a blunt introducing tip configured to protect a nasal alar cartilage of the patient from injury during insertion of the shafts into the nasal cavity.

14. The surgical assembly of claim 11, wherein each shaft has a straight medial surface complementing a shape of a septum of the nasal cavity, a curved lateral surface complementing a shape of an inferior concha of the nasal cavity, and an inferior surface configured to press against a palate of the nasal cavity, wherein, when sliding the inferior surface of each shaft on the palate of the nasal cavity, each curved lateral surface of each shaft is positioned adjacent to a respective inferior concha.

15. The surgical assembly of claim 11, wherein the limiting bridge is configured to limit dilation of the shafts to less than or equal to a dilation limit between nostrils of the patient.

16. The surgical assembly of claim 11, wherein the limiter is configured to limit collapsing of the handles, wherein the shafts are prevented from dilating beyond a dilation limit between each nostril of the patient.

17. The surgical assembly of claim 11, wherein each shaft includes a conduit configured to receive an endoscope.

18. The surgical assembly of claim 11, wherein the first bend angle of the bend portion is configured to prevent injury to a nasal dorsum of the patient and the second bend angle of the bend portion is configured to prevent injury to a lower alar cartilage of the patient.

19. The surgical assembly of claim 11, wherein each shaft further includes an endoscope configured to view a surgical field at the distal end of each shaft.

20. The surgical assembly of claim 19, wherein the endoscope is configured to connect wirelessly to a display.

* * * * *